United States Patent [19]

Chen

[11] Patent Number: 5,334,534
[45] Date of Patent: Aug. 2, 1994

[54] ENZYMATIC PREPARATION OF OPTICALLY ACTIVE PROPANOLOL AND β-ADRENERGIC BLOCKERS USING ESTERASE

[75] Inventor: Ching-Shih Chen, Wakefield, R.I.

[73] Assignee: The Board of Governors for Higher Education, State of Rhode Island and Providence Plantations, Providence, R.I.

[21] Appl. No.: 868,987

[22] Filed: Apr. 15, 1992

[51] Int. Cl.$^5$ ............................................. C12P 41/00
[52] U.S. Cl. ................................................. 435/280
[58] Field of Search ..................................... 435/280

[56] References Cited

FOREIGN PATENT DOCUMENTS 62-151196  7/1987  Japan .............................. C12P 41/00

OTHER PUBLICATIONS

Shieh W., JCS Chem Comm. 9:651–3 (1991).
Sagai T., J. Org Chem. 55:4643–47 (1990).
Sonnet P., Lipids 26:295–300 (1991).

*Primary Examiner*—Douglas W. Robinson
*Assistant Examiner*—S. Saucier
*Attorney, Agent, or Firm*—Samuels, Gauthier & Stevens

[57] ABSTRACT

A computer modeling approach is taken to delineate the structural requirements of substrate molecules for biocatalytic turnover and enantioselective discrimination. This leads to an efficient enzymatic preparation of optically active propranolol. The acyl-sustituents on the alcohol and the secondary amine of propranolol play crucial roles in controlling the catalysis and enantiospecificity, respectively, of the enzymatic hydrolysis.

2 Claims, 2 Drawing Sheets

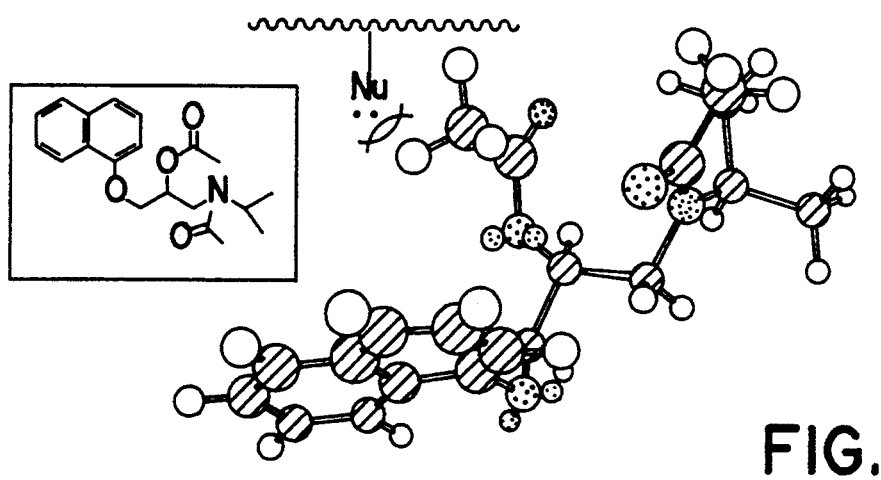
FIG. IA
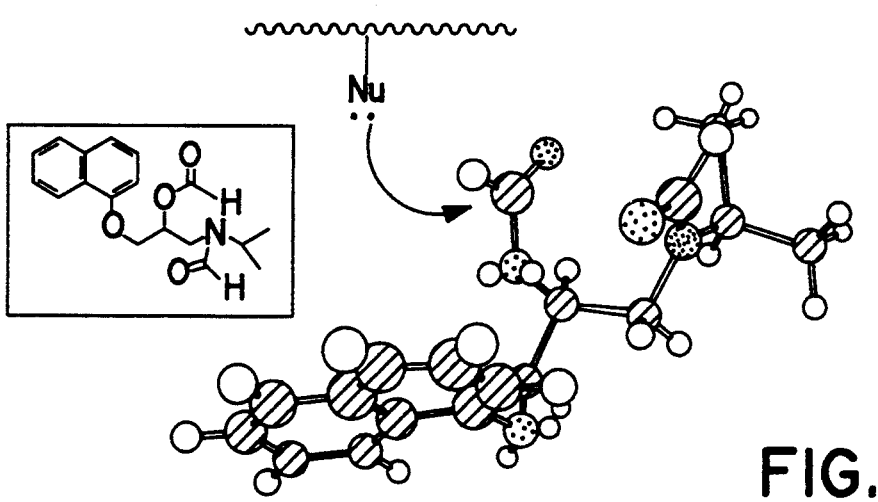
FIG. IB
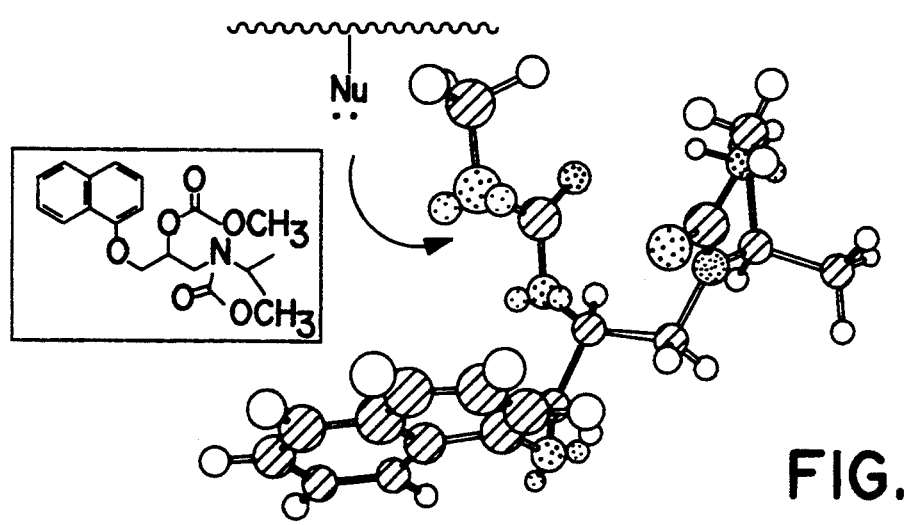
FIG. IC

ENZYMATIC PREPARATION OF OPTICALLY ACTIVE PROPANOLOL AND β-ADRENERGIC BLOCKERS USING ESTERASE

BACKGROUND AND BRIEF SUMMARY OF THE INVENTION

The advantages of applying enzymatic resolution to the preparation of optically active molecules have become well recognized. However, as the structure-activity correlations of most enzymatic reactions remain to be explored, predictions of the catalytic efficiency and stereochemical preference for a particular compound prove to be difficult; Sih, C. J.; Gu, Q. M.; Reddy, D. R. in Trends in Medicinal Chemistry, Mutschler E., Winterfieldt, E. Eds.; VCH, New York, 1987; pp. 181 and Kazlauskas, R. J.; Weissfloch, A. N. E.; Rappaport, A. T.; Cuccia, L. A. J. Org. Chem. 1991, 56, 2656. Although, with the recent advent of protein crystallography and computer graphics, researchers are now able to scrutinize the conformation of biocatalytic domains; Brady, L.; Brzozowski, A. M.; Derewenda, Z. S.; Dodson, E.; Dodson, G.; Tolley, S.; Turkenburg, J. P.; Christiansen, L.; Huge-Jensen, B.; Norskov, L.; Thim, L.; Menge, U. Nature 1990, 343, 767; Winkler, F. K.; D'Arcy, A.; Hunziker, W. ibid, 771. The establishment of a complete database appears to be far from realization. Consequently, by and large, design of an enzyme substrate to optimize chemical/optical yields has been conducted on a trial-and-error basis.

For rational substrate design, computer-aided molecular modeling is used. This approach provides insight into the energy-minimized conformations of substrate molecules, and thus provides a viable means to identify steric factors crucial to catalytic turnover and/or enantiomeric differentiation.

The preferred embodiment of the invention will be described in reference to an efficient enzymatic access to optically active propranolol (1). Compound 1 was chosen as the model in light of two considerations: (a) as (S)-1 is the active antipode in block β-adrenergic receptors, the development of an efficient preparation merits attention; Backvail, J. E.; Bjorkman, E. E.; Bystrom, S. E. Tetrahedron Lett. 1982, 23, 943; Katsuki, T. Tetrahedron Lett. 1984, 25, 2821; Miyano S.; Lu, L. D. L.; Viti, S. M.; Sharpless, K. B. J. Org. Chem. 1985, 50, 4350; and Klunder, J. M.; Soo, Y. K.; Sharpless, K. B. ibid, 1986, 51, 3710 (examples of chemical asymetric synthesis) and Iriuchijima, S.; Keiyu, A.; Kojima, N. Agri. Biol. Chem. 1982, 46, 1593; Marsuo, N.; Ohno, N.; Tetrahedron Lett. 1985, 26, 5533; Fuganti, C.; Grasselli, P.; Seneci, P. F.; Servi, S. Tetraherdon Lett. 1986, 27, 2061; Terao, Y.; Murata, M.; Achiwa, K. Tetrahedron Lett. 1988, 29, 5173; and Wang, Y. F.; Chen, S. T.; Liu, K. K. C.; Wong, C. H. Tetrahedron Lett. 1989, 30, 1917 (enzymatically prepared precursors); and (b) previous attempts by a number of groups to effect direct enzymatic resolution of 1 have not been successful so far; Jpn. Kokai Tokyo Koho JP 62 151,196 (Chem Abstr. 1988, 108, 110832d); and Jpn. Kokai Tokyo Koho JP 63 94,992 (Chem Abstr. 1989, 110, 93558r).

BRIEF DESCRIPTION OF THE DRAWINGS

FIG. 1a is a computer generated diagram of N,O-diacetylpropranolol 2;

FIG. 1b is a computer generated diagram of N,O-diformylpropranolol 3;

FIG. 1c is a computer generated diagram of N,O-bis(-methoxycarbonyl)-propranolol 4 (Nu represents the nucleophilic residue in the catalytic site)

DESCRIPTION OF THE PREFERRED EMBODIMENT(S)

Figure 2:
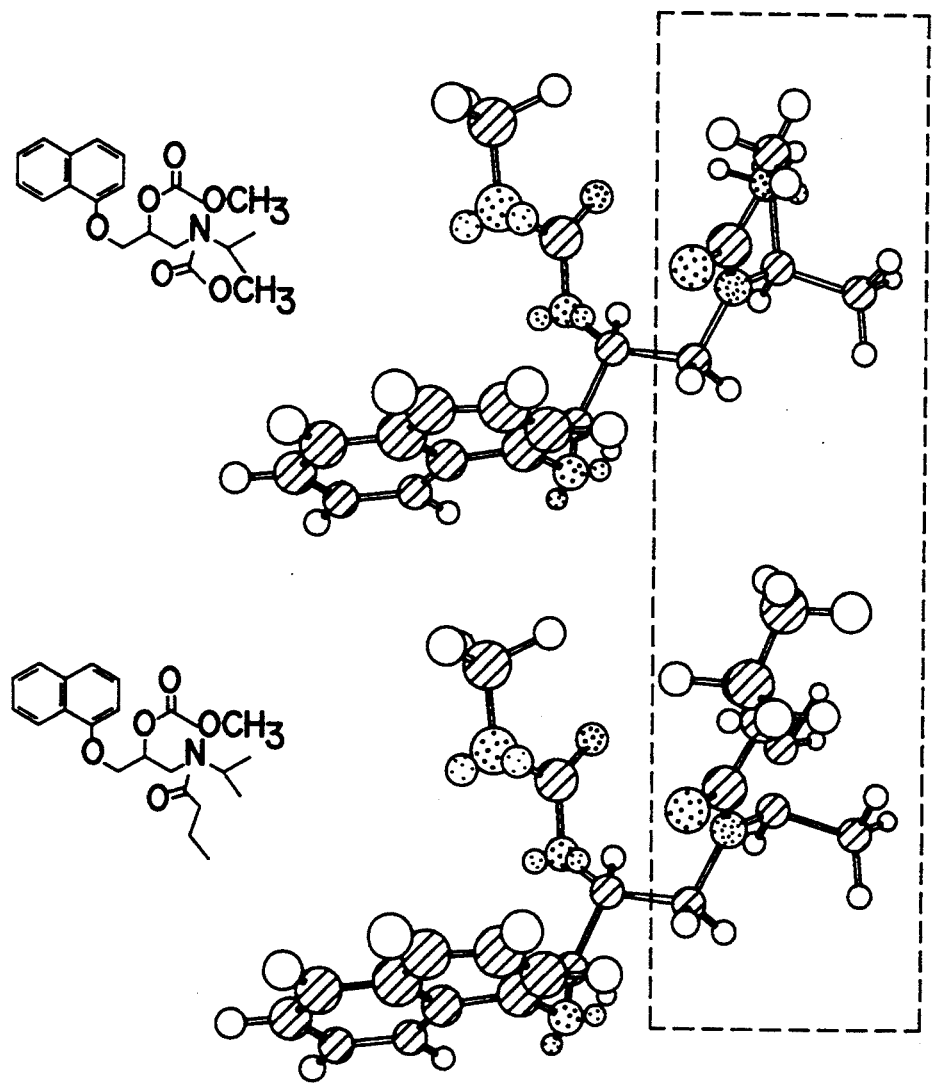
FIG. 2 is a comparison the energy-minimized confirmations of N,O-bis(methoxycarbonyl)-propranolol 4 and N-butyryl-O-methoxycarbonyl)-propranolol 8.

A variety of hydrolytic enzymes were examined for their enantioselective hydrolysis of the N,O-diacetyl derivative of 1 (rac-2).

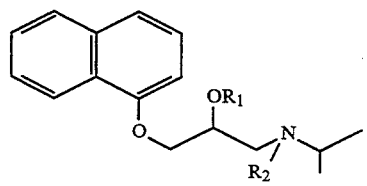

where
1: $R_1 = R_2 = H$
2: $R_1 = R_2 = C(O)CH_3$
3: $R_1 = R_2 = C(O)H$
4: $R_1 = R_2 = C(O)OCH_3$
5: $R_1 = R_2 = C(O)CH_2Cl$
6: $R_1 = R_2 = C(O)CCl_3$
7: $R_1 = R_2 = C(O)OC_2H_5$
8: $R_1 = C(O)OCH_3$  $R_2 = C(O)C_3H_7$ 9: $R_1 = C(O)OCH_3$  $R_2 = C(O)$ 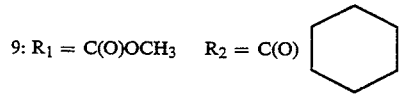

10: $R_1 = C(O)OCH_3$  $R_2 = C(O)C_7H_{15}$
11: $R_1 = C(O)OCH_3$  $R_2 = C(O)C_{11}H_{23}$

However, none of the enzymes tested (Proteases included: chymotrypsin, thermolysin and proteases from *Aspergillus oryzae, A. sojae, A. satoi, Rhizopus sp.,* and *Streptomyces caeapitosus.* Lipases included: crude lipase preparations from porcine pancrease, *Candida cylindracea, A. niger, Geotrichum candidum, Humicola lanuginosa, Mucor miehei, Pseudomonas sp., Rhizopus niveus,* and *R. oryzae.* Esterases included pig liver esterase, cholesterol esterase, and partially purified porcine pancreatic esterase) including lipases, proteases and esterases, were capable of effective deacylation of 2. This finding is in line with the previous results by other groups (Kirchner, G.; Scollar, M. P; Klibanov, A. M. J. Am. Chem. Soc. 1985, 107, 7071 and Sih, C. J.; personal communication). Presumably, the resistance to enzymatic cleavage stemmed from the intrinsic steric congestion that the cleavage site of 2, rendering the nucleophilic attack futile regardless of the conformations of biocatalytic sites. 2 was subjected to computer analysis using a commercial software (Chem3D plus ™) with a personal computer (Macintosh 11cx). FIG. 1a shows the energy-minimized conformation of 2 derived from the molecular mechanics calculation (Allinger's MM2 version).

As the naphthyl ring and the tertiary acetamide group may restrain the molecule from freely rotating in the enzyme pocket, the methyl moiety of the O-acetate represents a steric factor in hindering the nucleophilic displacement by interposing between the nucleophile and the carbonyl function. In principle, such steric congestion can be circumvented either by reducing the size of the acyl moiety or by removing the methyl group away from the nucleophile. Based on this principle, two potential candidates were selected for examination: N,O-diformyl-propranolol (3) and N,O-bix(methoxycarbonyl)-propranolol (4), respectively, whose energy-minimized conformations are presented in FIG. 1b and 1c, respectively. As shown, these two derivatives, especially the diformyl derivative 3, have the carbonyl function more accessible to the nucleophile as compared with 2.

3 and 4 were synthesized and subjected to enzymatic hydrolysis. As expected, both compounds were readily digested by various enzymes with different extents of enantiomeric discrimination, see Table 1 below. Relatively speaking, compound 3 was consumed at faster rates by a broader range of enzymes as compared with 4. Nearly all the enzymes examined were capable of hydrolyzing the O-formyl group at varying rates; whereas the ones cleaving the O-methoxycarbonyl group were limited to the esterases. This result agrees with the notion that an H atom poses less steric hindrance as compared with a methoxy group.

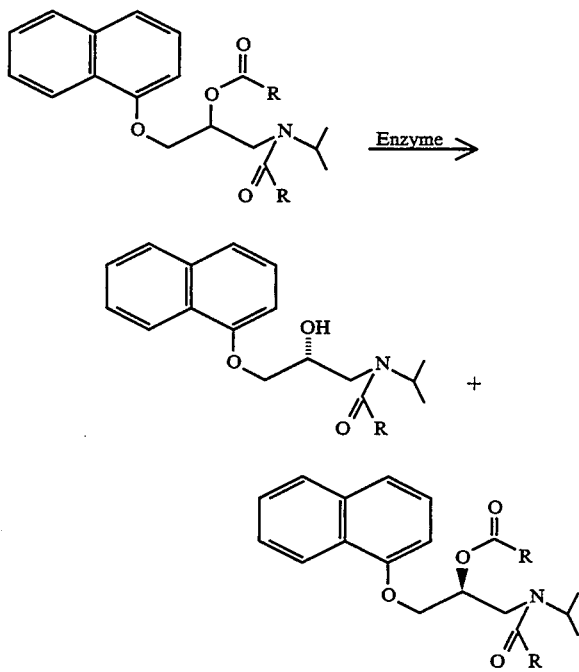

where ee(P) is the ee value of product (Chen, C. S., Fujimoto, Y.; Girdaukas, G.; Sih, C. J. J. Am. Chem. Soc. 1982, 104, 7294) ranged from 1 to 3. In addition, slow spontaneous hydrolysis of 3 in buffer solutions rendered this process unsuitable for preparative purposes. On the other hand, a partially purified esterase preparation from porcine pancreas acetone powder displayed moderate specificity (E=19) toward rac-4. This enzyme (PPE) appeared to be distinct from cholesterol esterase (CE) in light of the degree of enantiomeric specificity in hydrolyzing compound 4 (the E values were 5 and 19 for CE and PPE, respectively.)

However, the nature of these substituents (formyl and methoxycarbonyl) suggests that the rate enhancement can be attributed to the electron-withdrawing rather than the steric relaxation effect of these functions. In literature, activated esters (Kirchner, G.; Scollar, M. P.; Klibanov, A. M. J. Am. Chem. Soc. 1985, 107, 7071 and Gu, Q. M.; Chen, C. S.; Sih, C. J. Tetrahedron Ltt. 1986, 27, 1763) or formate esters (Bevinakatti, H. S.; Newadkar, R. V. Biotechnol. Lett. 1989, 11, 785) have been widely utilized to accelerate enzymatic hydrolysis and transesterification reactions. Consequently, to clarify this speculation, two activated esters, N,O-bis(chloroacetyl) and N,O-bis (trichloroacetyl) derivatives 5 and 6, respectively, were prepared and subjected to examination. Computer analysis showed that the extent of steric hindrance imposed by the chloromethyl groups was similar to that by the methyl counterpart in 2. In addition, it turned out that neither of them could be consumed by the enzymes even after prolonged exposure. This evidence clearly lent support to the conclusion from the computer modeling study that the O-acyl function assumed a crucial role in the catalytic step. Furthermore, it is noteworthy that N,O-bis(ethoxycarbonyl) propranolol (7) was not susceptible to hydrolysis by any of these enzymes, implying tightness in space around the vicinity of the nucleophile. This subtle structure-activity relationship appeared to arise from the complex enzyme-substrate interactions in conjunction with the relative restricted biocatalytic site.

This biocatalysis represented the first enzymatic access to 1 by direct kinetic resolution. Further elaboration on the substrate structure was conducted directed to two objectives: (a) to improve enzyme enantioselectivity, and (b) to define the shape of the biocatalytic site. In view of the importance of the O-methoxycarbonyl

TABLE I

| R | Enzyme | Stereochemical preference | Product Conversion (%) | Enantiomeric Excess | | E |
|---|---|---|---|---|---|---|
| | | | | Product (%) | Substrate (%) | |
| —H | PLE | R | 64 | 3 | 19 | 1.03 |
| (3) | CE | R | 53 | 26 | 29 | 2.2 |
| | PPE | R | 87 | 29 | 52 | 2.9 |
| —OCH$_3$ | PLE | R | 35 | 11 | 6 | 1.3 |
| (4) | CE | R | 38 | 56 | 35 | 5.0 |
| | PPE | R | 40 | 83 | 55 | 19.0 |

However, deacylation of 3 afforded products with low optical purity (<30% e.e.) as a result of poor enantioselectivity. The E value enantiomeric ratio is defined as the ratio of the specificity constants of the two enantiomers, $(k_{cat}/K_m)_S/(k_{cat}/K_m)_R$, and the value is calculated from $$E = ln[1-c(1+ee(P))]/ln[1-c(1-ee(P)],$$

function in catalytic turnover, the N-acyl site was targeted for further modification. Computer graphics of various N-acyl-O-methoxycarbonyl derivatives 8-11 revealed that the structures of these compounds closely resembled that of 3 except in the N-acyl region. A representative example is shown in FIG. 2 which compares the conformation of 8 to that of 3. As the local structures about the cleavage sites of these molecules were virtually superimposable, it was assumed that these substituents exerted influence upon the biocatalysis mainly in the enzyme-substrate (E-S) complexation but not in the nucleophilic attacking step. Based on the following simplified mechanism for enzymatic resolution (scheme 1).

(Scheme1)

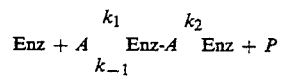

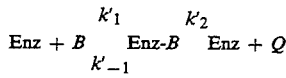

kinetic simulations include that high enantiospecificity [$(k_{cat}/K_m)_A(K_{cat}/K_m)_B$] connotes rapid and reversible E-S complexation (i.e. $k_{-1} \gg k_2$ and $k'_{-1} \gg k''_2$) (Sih, C. J.; Chen, C. S. Angew. Chem. Int. Ed. Engl. 1984, 23, 570 and Wang, Y. F.; Chen, C. S.; Girdaukas, G.; Sih, C. J. in Enzymes in Organic synthesis, Battersby, A. R., ed.; Pitman, London, 1985; pp. 128). Therefore, altering the N-acyl function leads to better enantiomeric selection by destabilizing the E-S complex. The steric effect of various substituents on enantioselectivity in a qualitative manner can be assessed and the conformation of the biocatalytic domain can be perceived.

Enantioselective deacylation of 8-11 were examined using the partially purified pancreas esterase (PPE) and crude pancreas acetone powder, respectively. N-Acyl-O-methoxycarbonyl derivatives could be readily prepared by treating 1 with equivalent amounts of the corresponding acyl chloride, followed by dimethyl pyrocarbonate. As expected, these compounds were also susceptible to hydrolytic cleavage with rates comparable to that of 3. The stereochemical outcomes of these reactions are summarized in Table 2 below.

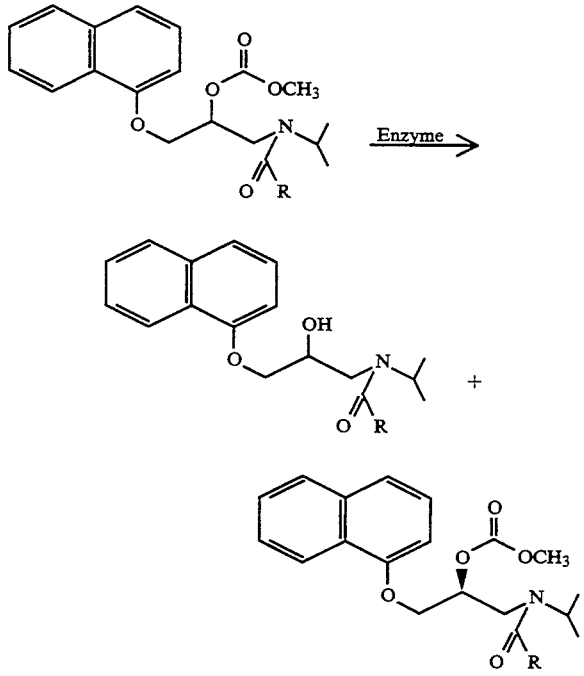

TABLE 2

| R | Enzyme | Stereochemical preference | Conversion (%) | Enantiomeric Excess Product (%) | Enantiomeric Excess Substrate (%) | E |
| --- | --- | --- | --- | --- | --- | --- |
| —$C_3H_7$ (8) | PPE | R | 29 | 96 | 41 | 76 |
|  | PPAP | R | 47 | 91 | 82 | 54 |
| (9) | PPE | R | 27 | 94 | 35 | 41 |
|  | PPAP | R | 33 | 72 | 35 | 8.6 |
| —$C_7H_{15}$ (10) | PPE | R | 40 | 77 | 34 | 12 |
| —$C_{11}H_{23}$ (11) | PPE | R | 23 | 81 | 25 | 12 |

As shown, the stereochemical preference was maintained despite great variation in the size of the acyl groups and the degree of enantiomeric discrimination differed considerably.

It was found that substitution of the methoxycarbonyl group with butyryl and cyclohexylcarbonyl functions give rise to marked improvement in enantiomeric selection, but long chain substituents led to lower specificity. With PPE, the observed E values were 19, 41, and 76 for 3, 8 and 9, respectively; whereas the E values for $C_8$ and $C_{12}$ acyl derivatives declined as compared with that of 3, 12.4 and 11.8, respectively, vs. 19. As expected, the partially purified esterase appeared to be more enantiospecific than the crude acetone powder because of the removal of competing enzymes. Nonetheless, the crude enzyme mediated-resolution still afforded a highly efficient process for the preparation of optically active 1. For instance, incubation for racemic 8 (10 g) and the crude aceton powder (5 g) for 120 h (47% conversion) gave (R)-N--butyryl propranolol and (S)-8 with optical purity of 91% and 82% e.e., respectively. Removal of the protecting groups in both compounds by alkaline hydrolysis, followed by recrystallization, afforded (R)- and (S)-1 with enantiomeric excess greater than 95 and 92%, respectively.

This computer modeling approach embodying the invention is useful in assessing the structure-activity relationships of biocatalytic reactions when their chemical and/or optical yields need to be enhanced. In addition, the experimental results obtained provide insite into the conformation of the enzyme active site. In view of the subtle steric effect on enzyme activity by the acetyl and the ethoxycarbonyl functions, the space surrounding the nucleophile appears to be highly restricted. In turn, this catalytic center is flanked by two large domains which can accommodate the naphthyl and tertiary amide, respectively.

EXAMPLES $^1$H NMR spectroscopy was carried out on a Bruker AM-300 spectrometer for solutions in deuteriochloroform with tetramethylsilane as the internal standard. Optical rotations were determined with a Rudolph Autopol 111 polarimeter for solutions in the indicated solvent. High-pressure liquid chromatography was performed using a Model 501 pump (Water Associates). Cholesterol esterase, pig liver esterase and porcine pancrease acetone powder were purchased from Sigma Chemical Co., and the enzyme units were defined accordingly. Other enzymes mentioned in the paper were obtained from either Amamo Enzyme Co. or Sigma Chemical Co. All other chemicals and solvents of the highest quality grade available were purchased from Aldrich Chemical Co. or Sigma Chemical Co.

Molecular Modeling: The computer analysis was carried out using the Chem3D plus ™ molecular modeling program (Cambridge Scientific Computing, Inc., Cambridge, Mass.) with a Macintosh 11cx personal computer. For any putative substrate, a computer graphic display of the possible conformation was drawn and subjected to energy minimization through molecular mechanics calculation. This minimum RMS gradient was set at 0.001, and the energy-minimized conformation could normally be obtained after 100 iterations.

N,O-Diacyl propranolols 2,5,6: The corresponding acyl chloride (22.8 mmol) was added dropwise to ice-cooled $CH_2Cl_2$ (20 ml) containing DL-propranolol (1) (2 g, 7.6 mmol) and triethylamine (2.3 g, 22.8 mmol). The resulting mixture was stirred at room temperature for 1 h, and was then washed successively with equal volumes of saturated aq. sodium bicarbonate, and brine. The organic layer was dried over sodium sulfate, and evaporated under reduced pressure. Purification of the crude residue over a silica gel column (hexane-ethyl acetate, 5:1 to 1:1) afforded the product. The yields ranged from 80–90%.

N,O-Diformyl propranolol 3: DL-1 (2 g, 7.6 mmol) was refluxed with formic acid (30 ml) for 12 h. The remaining formic acid was removed under reduced pressure. Purification of the crude residue over a silica gel column (hexane-ethyl acetate, 5:1 to 2:1) yielded 400 mg (16%) of the diformyl derivative 3. H (300 MHz) 1.18–1.35 (6 H, m), 3.34–3.50 (1 H, m), 3.54–3.84 (4 H, m), 4.22–4.36 (1 H, m), 6.80–8.20 (8 H, m), 8.27 (1 H, s).

N-O-dimethoxycarbonyl propranolol 4: DL-1 (2 g, 7.6 mmol) was stirred with dimethyl pyrocarbonate (10.9 g, 76 mmol) in the presence of catalytic amounts of N,N-dimethyaminopyridine (DMAP) at 60° C. for 12 h. To the solution was added 20 ml of ethyl acetate, and the mixture was washed successively with equal volumes of saturated aq. sodium bicarbonate, 1 M HCl, and brine. The organic layer was dried over sodium sulfate, and evaporated under reduced pressure. Purification of the crude residue over a silica gel column (hexane-ethyl acetate, 5:1 to 2:1) afforded 2 g (75%) of 4. 1H NMR $_H$(300 MHz) 1.0–1.8 (6 H, m), 3.2–3.6 (1 H, m), 3.63 (3 H, s), 3.77 (3 H, s), 3.8–4.6 (4 H, m), 5.3–5.6 (1 H, m), 6.68–7.0 (1 H, m), 7.1–7.9 (5 H, m), 8.1–8.3 (1H, m).

N-acyl-O-methoxycarbonyl propranolols 8–12: The corresponding acyl chloride (7.6 mmol) was added dropwise to ice-cooled $CH_2Cl_2$ (20 ml) containing 1 (2 g, 7.6 mmol) and triethylamine (0.93 g, 9.12 mmol). The resulting mixture was stirred at room temperature for 30 min, and was washed successively with sodium bicarbonate and brine. The organic layer was dried over sodium sulfate, and evaporated under reduced pressure. The oily residue was mixed with dimethyl pyrocarbonate (5 ml), and to the residue was added catalytic amounts of DMAP. The mixture was stirred at 50° C. for 12 h. The workup procedure was basically the same as described above. Purification of the crude residue over a silica gel column (hexane-ethyl acetate, 10:1 to 2:1 depending on the compound applied) afforded products with yields ranging from 75 to 85%. 1H NMR $_H$(300 MHz) 8: 0.88–1.00 (3 H, m), 1.19– 1.31 (6 H, m), 1.62–1.75 (2 H, m), 2.28–2.53 (2 H, m), 3.32–3.35 (1 H, m), 3.78 (3 H, s), 3.80–3.89 (1 H, m), 4.02–4.19 (1 H, m), 4.27–4.39 (2 H, m), 5.45–5.52 (1 H, m), 6.72–6.81 (1 H, m), 7.32–7.81 (1 H, m), 8.21–8.25 (1 H, m); 9: 1.18–1.37 (10 H, m) 1.45–1.81 (6 H, m), 2.47–2.57 (1 H, m), 3.36–3.51 (1 H, m) 3.77 (3 H, s), 3.79–3.88 (3 H, m), 4.13–4.22 (1 H, m), 4.26–4.37 (2 H, m), 5.44–5.51 (1 H, m), 6.78 (1 H, d, J =7.4 Hz), 7.32 (4 H, m), 7.76–7.82 (1 H, m), 8.221–8.25 (1 H, m); 10: 0.5–1.9 (19 H, m), 2.2–2.5 (2 H, m), 3.4–3.7 (2 H, m), 3.8–4.3 (3 H, m), 3.7 (3, H, s), 5.2–5.5 (1 H, m), 6.7–6.9 (1 H, m), 7.1–7.5 (4 H, m), 7.5–8.0 (1 H, m), 8.0–8.3 (1 H, m); 11: 0.5–2.1 (27 H, m), 2.2–2.5 (2 H, m), 3.2–3.5 (2 H, m), 3.7 (3 H, s), 3.8–4.5 (3 H, m), 5.2–5.5 (1 H, m), 6.6–6.8 (1 H, m), 7.1–7.5 (4 H, m), 7.6–7.8 (1 H, m), 7.9–8.3 ( 1 H, m) .

Partial purification of porcine pancrease acetone powder: Porcine pancreatic acetone powder (Sigma, 10 g) was suspended in 50 ml of 10 mM potassium phosphate buffer (pH 7.0) (buffer A), and subjected to homogenization. The tissue debris was removed by centrifugation at 12,000×g for 20 min, and the supernatant was dialyzed against 3 L of buffer A for 12 h. The solution was then applied to a DEAE-Sepharose CL-6B column (5×10 cm) equilibrated with buffer A. The column was washed with 200 ml of buffer A, and eluted with a linear gradient (600 ml) consisting of 0.01 to 0.5 M NaCl in buffer A. Fractions of 6 ml were collected. The esterase activity was assayed using p-nitrophenyl acetate as the substrate. Fractions 110 to 132, which contained the esterase, were collected, and the pooled solution was used for the enzyme reaction. One unit of PPE is that amount of enzyme catalyzing the hydrolysis of 1 $\mu$mol of p-nitrophenyl acetate per min at 25° C.

Enzyme incubations: The substrate (200 mg), dissolved in DMF (0.5 ml), was introduced to 0.1 M-potassium phosphate buffer (20 ml; pH 7.0) containing 0.5% Tween 80. To the mixture was added 200, 20, 20 units of PLE, CE, and PPE, respectively. The vigorously stirred mixture was incubated at 25° C. and the progress of the reaction was monitored by silica gel TLC analysis (hexane-ethyl acetate, 3:1 to 1:1, depending on the compound). After 2–120 h, the reaction was quenched by extracting the mixture with an equal volume of ethyl acetate (x3). The combined extracts were dried over sodium sulfate, and concentrated to dryness. The residue was chromatographed over a silica gel column (hexane-ethyl acetate) to afford the N-acyl propranolol and the remaining substrate for optical purity determination.

Enantiomeric Purity Determination: The N-acyl propranolols obtained from the biotransformation, with the exception of N-formyl propranolol, were treated with (S)-(−)-2-methoxy-2-(trifluoromethyl)-2-henylacetyl (MPTA) chloride to form the corresponding (−)-MPFA esters. The MPTA derivatives were analyzed by HPLC using a silica gel column (4.6 mm×25 cm) using hexane-ether, 3:1, as the mobile phase. The flow rates for individual MPFA esters, and the corresponding retention times were, respectively: N-methoxycarbonyl: 1.2 ml/min; S: 40 min, R: 43.6 min; N-butyryl: 1.2 ml/min; S: 25.6 min, R: 27 min; N-cyclohexanecarbonyl: 2 ml/min; S: 12.5 min, R: 13.5 min; N-octanoyl: 1.0 ml/min; S: 25.5 min, R: 29.7 min; N-dodecanoyl: 0.5 ml/min; S: 45.5 min, R: 53 min. To determine the optical purity of the N-formyl derivative, the compound was treated with alkaline, followed by (−)MPTA chloride to form the N,O-di-MPTA derivative. The retention times were 33.3 min and 31.3 min for the S and R isomers, respectively, at a flow rate of 1.5 ml/min. With regard to the remaining substrate fraction, the compounds were treated with 1N KOH/CH₃OH at room temperature for 30 min to yield the corresponding N-acyl propranolols. The optical purity could thus be determined according to the aformentioned procedure.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described my invention, what I now claim is:

1. A method for the synthesis of an enzymatic optically active propranolol which comprises:

effecting an enzyme mediated enantioselective hydrolysis on a substrate of the formula:

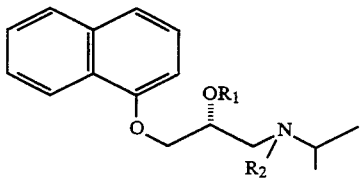

where
$R_1 = R_2 = C(O)H$
$R_1 = R_2 = C(O)OCH_3$
$R_1 = C(O)OCH_3$  $R_2 = C(O)C_3(O)C_3H_7$

$R_1 = C(O)OCH_3$  $R_2 = C(O)C_7H_{15}$
$R_1 = C(O)OCH_3$  $R_2 = C(O)C_{11}H_{23}$; and wherein
the hydrolytic enzyme is cholesterol esterase, pig liver esterase or porcine pancrease esterase to form the corresponding (R) and (S) enantiomers;
separating the diasteroisomers; and
recovering the separated diasteroisomers.

2. The method of claim 1 which includes: converting the separated (S) enantiomer to

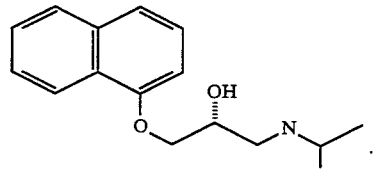

* * * * *